US00RE48968E

(19) United States
(12) Reissued Patent
Milam et al.

(10) Patent Number: US RE48,968 E
(45) Date of Reissued Patent: Mar. 8, 2022

(54) WIRELESS EARBUDS AND RELATED METHODS

(71) Applicant: Skullcandy, Inc., Park City, UT (US)

(72) Inventors: James Milam, Heber, UT (US); Peter M. Kelly, Tustin, CA (US); David G. Vogt, Jr., Salt Lake City, UT (US); Steve Page, Salt Lake City, UT (US); Ryan Jung, Holladay, UT (US)

(73) Assignee: Skullcandy, Inc., Park City, UT (US)

(21) Appl. No.: 16/401,796

(22) Filed: May 2, 2019

Related U.S. Patent Documents

Reissue of:
(64) Patent No.: 9,900,680
Issued: Feb. 20, 2018
Appl. No.: 15/342,841
Filed: Nov. 3, 2016

U.S. Applications:
(60) Provisional application No. 62/253,250, filed on Nov. 10, 2015.

(51) Int. Cl.
*H04R 1/10* (2006.01)
*A61B 5/00* (2006.01)

(52) U.S. Cl.
CPC ..... *H04R 1/1041* (2013.01); *A61B 5/0015* (2013.01); *A61B 5/486* (2013.01);
(Continued)

(58) Field of Classification Search
None
See application file for complete search history.

(56) References Cited

U.S. PATENT DOCUMENTS 6,370,401 B1 * 4/2002 Baranowski ..... H02G 11/02 455/348
6,424,820 B1 * 7/2002 Burdick ..... H04B 5/0081 455/132

(Continued)

FOREIGN PATENT DOCUMENTS

EP 2506597 A1 10/2012
WO 2012/024656 A2 2/2012
WO 2016/032011 A1 3/2016

OTHER PUBLICATIONS

European Search Report for European Application No. 16197949.7 dated Apr. 6, 2017, 8 pages.

(Continued)

*Primary Examiner* — John M Hotaling
(74) *Attorney, Agent, or Firm* — TraskBritt

(57) ABSTRACT

A wireless earbud system includes a first earbud assembly and a second earbud assembly. Each of the first earbud assembly and the second earbud assembly include a housing, an audio driver disposed within the housing, and a wireless receiving unit operatively coupled to the audio driver. The wireless receiving unit is configured to receive a wireless data signal and drive the audio driver based on audio data transmitted in the wireless data signal. The wireless earbud system may also include a tether with a first end and a second end. The first end of the tether is configured to removably couple to the first earbud assembly by a first detachable connector, and the second end of the tether is configured to removably couple to the second earbud assembly by a second detachable connector. Methods also relate to the wireless earbud system.

38 Claims, 6 Drawing Sheets

(52) U.S. Cl.
CPC ..... *A61B 5/6803* (2013.01); *H04R 1/1016* (2013.01); *H04R 1/1025* (2013.01); *H04R 1/1033* (2013.01); *H04R 1/1058* (2013.01); *H04R 2420/05* (2013.01); *H04R 2420/07* (2013.01)

(56) References Cited

U.S. PATENT DOCUMENTS

| | | | | |
|---|---|---|---|---|
| 8,515,115 | B2 * | 8/2013 | Kelly | H04R 1/1016 381/370 |
| 9,210,498 | B1 * | 12/2015 | Shaffer | H02J 7/342 |
| 9,532,126 | B1 * | 12/2016 | Kelly | H04R 1/1016 |
| 9,579,060 | B1 * | 2/2017 | Lisy | A61B 5/0533 |
| 9,635,696 | B1 * | 4/2017 | Liu | H04W 76/28 |
| 2005/0136839 | A1 | 6/2005 | Seshadri et al. | |
| 2006/0286933 | A1 * | 12/2006 | Harkins | H04B 1/385 455/41.2 |
| 2008/0242229 | A1 * | 10/2008 | Sharma | H04M 1/05 455/41.3 |
| 2009/0097689 | A1 | 4/2009 | Prest et al. | |
| 2009/0154739 | A1 * | 6/2009 | Zellner | H04R 1/1041 381/311 |
| 2010/0000054 | A1 * | 1/2010 | Roser | H04R 1/1091 24/3.12 |
| 2010/0166207 | A1 | 7/2010 | Masuyama | |
| 2012/0027215 | A1 * | 2/2012 | Sim | H04R 1/1041 381/55 |
| 2012/0058727 | A1 | 3/2012 | Cook et al. | |
| 2012/0230510 | A1 * | 9/2012 | Dinescu | H04R 5/033 381/80 |
| 2013/0250135 | A1 * | 9/2013 | Blum | H04N 5/23203 348/211.99 |
| 2013/0256345 | A1 * | 10/2013 | Larkin | H04R 1/105 224/201 |
| 2014/0072137 | A1 * | 3/2014 | Nelson | H04R 1/1041 381/74 |
| 2014/0192995 | A1 | 7/2014 | Cataldo et al. | |
| 2014/0219467 | A1 * | 8/2014 | Kurtz | H04R 3/12 381/74 |
| 2015/0092972 | A1 * | 4/2015 | Lai | H04R 1/1008 381/333 |
| 2015/0230019 | A1 * | 8/2015 | Sakai | H04R 1/1041 381/74 |
| 2015/0272305 | A1 * | 10/2015 | Howard | A45F 5/02 29/428 |
| 2015/0365757 | A1 * | 12/2015 | Abreu | H04R 1/1066 381/381 |
| 2016/0014492 | A1 * | 1/2016 | McCarthy | H04R 1/1091 381/74 |
| 2016/0029114 | A1 * | 1/2016 | Chen | H04R 1/1041 381/74 |
| 2016/0073188 | A1 * | 3/2016 | Linden | H04R 1/1025 381/309 |
| 2016/0073189 | A1 * | 3/2016 | Linden | H04R 1/1025 381/74 |
| 2016/0182991 | A1 * | 6/2016 | Zakzeski | H04R 1/1091 381/381 |
| 2016/0330541 | A1 * | 11/2016 | Miao | H04R 1/1041 |
| 2016/0379659 | A1 * | 12/2016 | Negi | H04L 25/49 381/74 |
| 2017/0064427 | A1 * | 3/2017 | Rich | H04R 1/1025 |
| 2017/0094399 | A1 * | 3/2017 | Chandramohan | A45C 13/02 |
| 2017/0134845 | A1 * | 5/2017 | Milam | H04R 1/1041 |

OTHER PUBLICATIONS

Extended European Search Report for European Application No. 16197949 dated Jul. 31, 2017, 14 pages.

* cited by examiner

WIRELESS EARBUDS AND RELATED METHODS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: This is a broadening reissue application of U.S. Pat. No. 9,900,680 B2, issued Feb. 20, 2018, to Milam et al. for WIRELESS EARBUDS AND RELATED METHODS.*

CROSS-REFERENCE TO RELATED APPLICATION

This application claims the benefit of U.S. Provisional Patent Application Ser. No. 62/253,250, filed Nov. 10, 2015, the disclosure of which is hereby incorporated herein in its entirety by this reference.

TECHNICAL FIELD

The present disclosure relates generally to earbud headphones, and more specifically to earbuds configured to receive a wireless data signal from a media device.

BACKGROUND

Earbud headphones are used to convert an electronic signal into an audible sound, which is transmitted to the ear of a person using the earbud headphones. Earbud headphones are used in conjunction with many different types of electronic devices, such as media players, hearing aids, cellular telephones, televisions, computers, etc. In contrast to what are referred to in the industry as "on-ear" headphones and "over-ear" headphones, earbud headphones are relatively small headphones that rest within the concha of the outer ear and are often referred to as "in-ear" headphones. Earbud headphones are retained in place by the cooperation and mechanical interference between the earbud headphone and the ear of the user. Some earbud headphones include a portion that is sized and configured to extend from a main body of the headphone into the external auditory canal of the ear.

Earbud headphones are popular among users because they are generally relatively small and portable. Moreover, when a user is participating in various activities, earbud headphones interfere to a much lesser extent with the other accessories or equipment of the user, such as helmets, goggles, hats, and headbands compared to on-ear and over-ear headphones, which often include a headband or other connecting structure (in addition to wiring) extending around the head of the user between each headphone.

Some earbud headphones may include wireless functionality. For example, data from a media player may be transmitted by radio frequency (RF) signals from a media device to a wireless earbud. Wireless protocols such as Wi-Fi, BLUETOOTH®, or other protocols may be used for wireless transmission.

BRIEF SUMMARY

In some embodiments, a wireless earbud system includes a first earbud assembly and a second earbud assembly. Each of the first earbud assembly and the second earbud assembly includes a housing, an audio driver disposed within the housing, and a wireless receiving unit operatively coupled to the audio driver. The wireless receiving unit is configured to receive a wireless data signal and drive the audio driver based on audio data transmitted in the wireless data signal. The wireless earbud system further includes a tether with a first end and a second end. The first end of the tether is configured to removably couple to the first earbud assembly by a first detachable connector, and the second end of the tether is configured to removably couple to the second earbud assembly by a second detachable connector.

In other embodiments, a wireless earbud system includes a first earbud assembly and a second earbud assembly. Each of the first earbud assembly and the second earbud assembly include an audio driver, a wireless receiving unit operatively coupled to the audio driver, the wireless receiving unit configured to receive a wireless data signal, and an earbud battery configured to supply power to one or both of the audio driver and the wireless receiving unit. The wireless earbud system also includes a tether including a first end with a first detachable connector configured to mechanically and electrically couple the first end of the tether to the first earbud assembly, and a second end with a second detachable connector configured to mechanically and electrically couple the second end of the tether to the second earbud assembly. The tether also includes an electronic control unit disposed intermediate the first end of the tether and the second end of the tether. The electronic control unit includes a wireless unit configured to receive a wireless data signal from a media device and to transmit an audio signal based on the wireless data signal through electrical conductors in the tether to the first and second earbud assemblies when the first and second earbud assemblies are coupled to the first and second ends of the tether, respectively, and an electronic control unit battery configured to supply power to the wireless unit.

In yet other embodiments, a method of forming a wireless earbud system includes forming an electronic control unit comprising a wireless unit, a battery, and a tether. The method also includes forming first and second wireless earbud assemblies, and configuring first and second ends of the tether to removably couple to the first and second wireless earbud assemblies. The method also includes configuring one or both of the first and second wireless earbud assemblies to receive a wireless signal from a media device and to drive audio drivers in the first and second wireless earbud assemblies with an audio signal based on data received from the media device when the first and second ends of the tether are decoupled from the first and second wireless earbud assemblies, and configuring the wireless unit of the electronic control unit to receive a wireless signal from the media device and to drive the audio drivers in the first and second wireless earbud assemblies through electrical conductors disposed within the tether with an audio signal based on data received wirelessly from the media device when the first and second ends of the tether are respectively coupled to the first and second earbud assemblies.

DETAILED DESCRIPTION

The illustrations presented herein are not meant to be actual views of any particular headphone or component thereof, but are merely idealized representations employed to describe various embodiments of the disclosure.

The disclosure relates to earbud headphones configured to communicate wirelessly (e.g., through radio frequency (RF) electromagnetic waves) with a media device. The earbud headphones may include a tether that mechanically and/or electrically couples the earbud headphones to one another. The earbud headphones may function differently when connected by the tether compared to when the earbud headphones are used without the tether.

Figure 1:
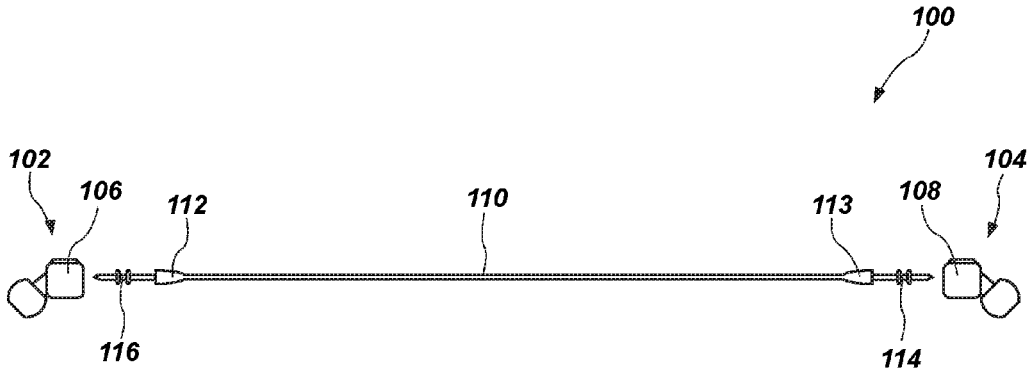
FIG. 1 is a plan view of an embodiment of an earbud system according to the disclosure.

FIG. 1 is a plan view of a wireless earbud system 100 according to the disclosure. The wireless earbud system 100 may include a first earbud 102 and a second earbud 104. The first earbud 102 and the second earbud 104 may include a first earbud housing 106 and a second earbud housing 108, respectively. The wireless earbud system 100 includes a tether 110 formed of a lightweight, flexible material, such as a woven fabric cord, a polymer (plastic, elastomeric, etc.) cord, etc. The tether 110 may include a first end 112 and a second end 113. The first end 112 and the second end 113 may include detachable connectors 114 and 116, respectively. The detachable connectors 114 and 116 may be configured to mechanically couple the first end 112 of the tether 110 to the first earbud 102, and the second end 113 of the tether 110 to the second earbud 104. For example, each of the detachable connectors 114 and 116 may include a plug configured for insertion into a corresponding recess of the first or second earbud 102, 104.

The first and second wireless earbuds 102 and 104 may be used in conjunction with the tether 110 to, e.g., prevent loss of an individual one of the first and second earbuds 102 and 104. In some embodiments, connection of the tether 110 may alter the functionality of the wireless earbuds, as described in detail below in connection with FIGS. 4, 5, and 6. In some embodiments, the detachable connectors 114 and 116 may not include electrical connections configured to establish electrical communication between the first and second wireless earbuds 102 and 104, such that the connections between the detachable connectors 114 and 116 and the first and second wireless earbuds 102 and 104 is only mechanical and not electrical. In such embodiments, the detachable connectors 114 and 116 may not comprise any electrically conductive material. In other embodiments, the detachable connectors 114 and 116 may include electrical connections configured to establish electrical communication between the first and second wireless earbuds 102 and 104 and circuitry within the tether 110. Such electrical connections are described in detail below in connection with FIGS. 10A and 10B.

Figure 2:
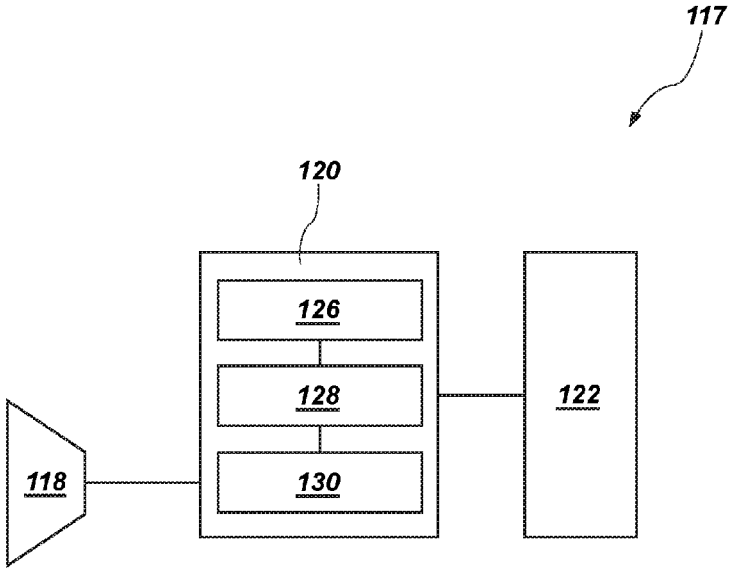
FIG. 2 is a schematic diagram of components of an earbud according to the disclosure.

FIG. 2 is a schematic representation of components 117 within an earbud headphone (e.g., the first earbud 102 or the second earbud 104 of FIG. 1). The components 117 within the earbud headphone may include, without limitation, an audio transducer 118, a wireless audio unit 120, and a battery 122. The audio transducer 118 may be an electromechanical device configured to receive an analog electrical signal containing audio information and convert the electrical energy to sound waves (e.g., physical vibrations with a frequency of about 20 Hz to about 20 kHz). In some embodiments, each of the first earbud 102 and the second earbud 104 may include a plurality of audio transducers 118. In some embodiments, each of the first earbud 102 and the second earbud 104 may include an enclosure tuned with respect to the audio transducer 118 to enhance (e.g., increase) the output of the audio transducer 118 within a particular range of frequencies. In addition, some embodiments may include a tuned port or a tuned diaphragm configured to enhance the output of the audio transducer 118 within a particular frequency range.

The wireless audio unit 120 may include circuitry configured to receive wireless signals and transmit wireless signals. The wireless audio unit 120 may also include circuitry configured to decode a digital wireless signal. For example, the wireless audio unit 120 may include circuitry configured to convert a digital signal to an analog audio signal. In one embodiment, the wireless unit may include an RF receiver 126 operatively coupled to a digital-to-analog converter (DAC) 128. An audio amplifier 130 may be operatively coupled to an analog output of the DAC 128 and configured to amplify the analog audio output from the DAC 128 to a level suitable to drive the audio transducer 118. The wireless audio unit 120 may also include an RF transmitter (not shown) configured to broadcast a wireless signal, as discussed below.

The battery 122 may be configured to supply electrical current to the wireless audio unit 120. In other words, current from the battery 122 may be consumed by the RF receiver 126, the DAC 128, and the audio amplifier 130. The battery 122 may be, for example, a rechargeable lithium-ion battery, or any other battery with suitable energy density.

In some embodiments, the first earbud 102 and the second earbud 104 may include components and circuitry to provide active noise cancelling (ANC) functionality. For example, each of the first earbud 102 and the second earbud 104 may include a microphone for converting ambient noises to electrical signals. Signal processing circuitry may generate electrical signals representing sounds identical to the ambient sounds but in opposite phase. The opposite-phase ambient sounds may be reproduced through the audio transducer 118 to cancel the ambient sounds.

Figure 3:
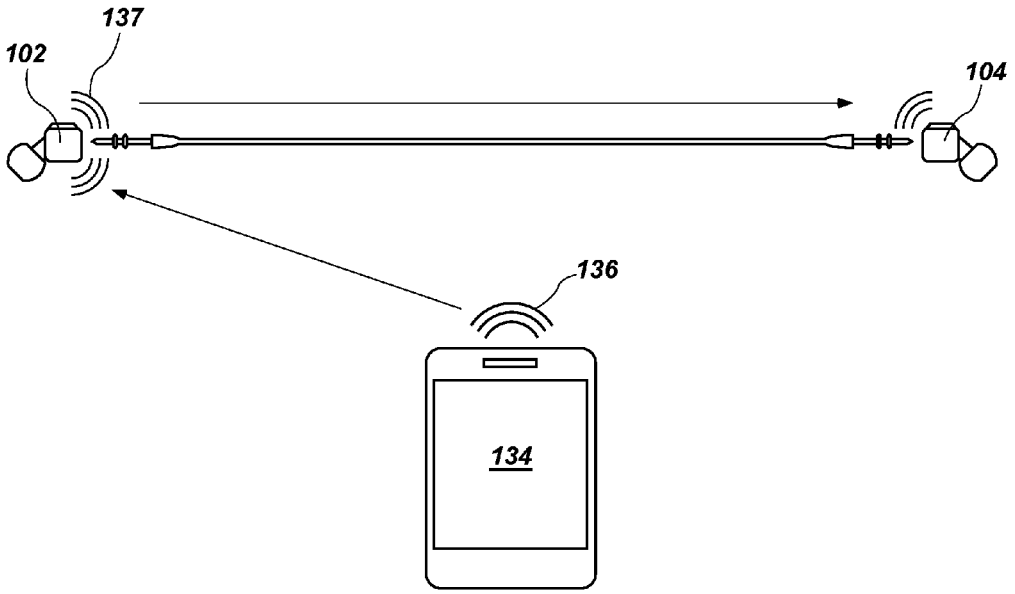
FIG. 3 is a schematic diagram showing operation of an earbud system according to the disclosure.

FIG. 3 is a schematic diagram showing an operational mode of the wireless earbud system 100 (FIG. 1). A media device 134 may be configured to broadcast a wireless signal 136 containing data representing an audio signal. The media device 134 may be, for example, a handheld device such as a cellular "smart" phone, a tablet computer, a digital music player, a laptop computer, a desktop computer, etc. In the embodiment shown in FIG. 3, the wireless earbuds 102 and 104 may operate in a so-called "master-slave" configuration. For example, one of earbuds 102 and 104 may be designated the master. An RF receiver in the master earbud (e.g., RF received 126 (FIG. 2) in the earbud 102) may receive the wireless signal 136 from the media device 134. The wireless signal 136 from the media device 134 may be separated into left and right audio channels by circuitry and/or software routines associated with the master earbud. Data from one audio channel (e.g., one of left or right) may be converted to an audio signal, amplified, and played through an audio transducer 118 (FIG. 2) in the master earbud. Data from the other audio channel (e.g., the other of the left or right channels) may be transmitted wirelessly (e.g., by wireless signal 137) from an RF transmitter within the master earbud to an RF receiver (e.g., RF receiver 126) within the slave earbud, where the data is converted to an audio signal, amplified, and played through an audio transducer 118 in the slave earbud.

Operation as the master earbud may consume significantly more power than operation as the slave earbud, as the master earbud must separate the channels and re-transmit one of the channels to the slave earbud. Accordingly, in some embodiments, each of the earbuds 102 and 104 may be configured to alternately function as master and slave. For example, the earbuds 102 and 104 may switch between master and slave roles on a regular, periodic basis to maintain generally equal battery charge between the earbud 102 and the earbud 104. In other embodiments, the particular earbud that functions as the master or slave may be chosen by other routines based on remaining charge in each battery and/or other parameters. Furthermore, while the above description assumes the earbuds 102 and 104 are functioning as a stereo pair, some data streams broadcast by the media device 134 may include only a single channel of audio data (i.e., monophonic sound). Such data may be received and played by one of the earbuds 102 and 104, or may be received and played simultaneously by both of the earbuds 102 and 104.

In some embodiments, the media device 134 may broadcast a wireless signal that is received directly by each of the first earbud 102 and second earbud 104. In other words, neither of the first earbud 102 and the second earbud 104 function as master or slave, but each receives the wireless signal 136 directly from the media device 134. When operating in this arrangement, each of the earbuds 102 and 104 convert a portion of the wireless signal 136 corresponding to one of the left or right channels to an analog audio signal (e.g., by processing a portion of the wireless signal 136 through the DAC 128 and audio amplifier 130) and play the audio signal through an audio transducer 118 (FIG. 2).

The wireless signal 136 may be broadcast by the media device 134 based on established wireless protocols, such as the BLUETOOTH® Advanced Audio Distribution Profile (A2DP). Additionally or alternatively, other wireless protocols (e.g., Wi-Fi), may be used.

Figure 4:
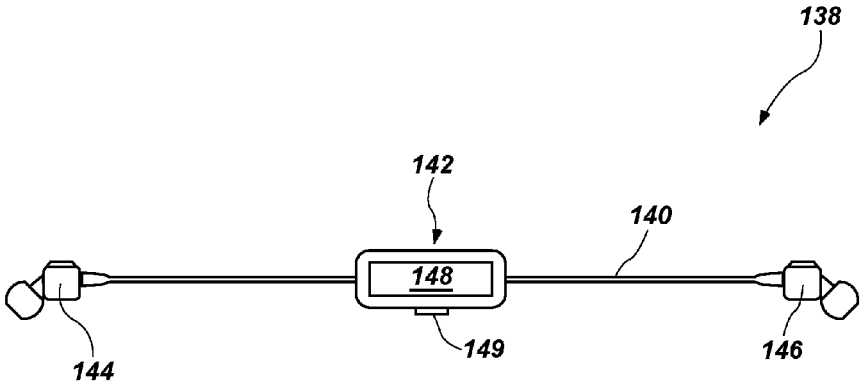
FIG. 4 is a plan view of another embodiment of an earbud system according to the disclosure.

FIG. 4 illustrates another embodiment of a wireless earbud system 138 according to the disclosure. In wireless earbud system 138, a tether 140 may include electronic components 142 configured to be operatively connected to (e.g., by electrically conductive contacts 219 described below in connection with FIGS. 10A and 10B) a first earbud 144 and a second earbud 146 when the first earbud 144 and the second earbud 146 are connected by the tether 140. For example, in the embodiment shown in FIG. 3, the electronic components 142 may include a battery 148 configured to provide power to operate one or more of the RF receiver 126 (FIG. 2), RF transmitter (not illustrated), DAC 128 (FIG. 2), and audio amplifier 130 (FIG. 2) of each of the earbuds 144 and 146 when the tether 140 is connected to the first earbud 144 and the second earbud 146. Furthermore, the battery 148 may be configured to charge (e.g., recharge) batteries (e.g., battery 122 described in connection with FIG. 2) in the wireless earbuds 144 and 146 when the tether 140 is connected to the first earbud 144 and the second earbud 146. When the tether 140 is connected to one or both of the first earbud 144 and the second earbud 146, the electronic componentry within the earbuds 144 and 146 may draw power from one or both of the battery 148 in the tether 140 and the batteries 122 within the individual earbuds 144 and 146. The battery 148 may be a lithium-ion rechargeable battery as discussed above, or a battery with different chemistry and/or construction. In some embodiments, the battery 148 may be charged by connecting a charging cable (e.g., micro USB, mini USB, USB-C) between a charging port 149 operatively coupled to the battery 148 and a power source (e.g., a USB port of a computer, charging station, etc.).

Figure 5:
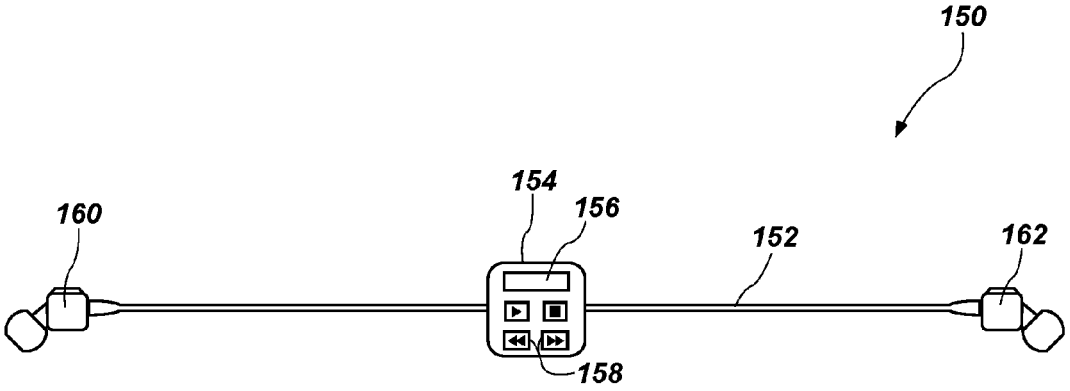
FIG. 5 is a plan view of yet another embodiment of an earbud system according to the disclosure.

FIG. 5 illustrates another wireless earbud system 150 in accordance with the present disclosure. In the embodiment of FIG. 5, a tether 152 may include an electronic control unit 154. The electronic control unit 154 may include, without limitation, one or more of a battery 156 similar to the battery 148 described in connection with FIG. 3, an RF receiver, an RF transmitter, a DAC, and an audio amplifier similar to those shown in connection with FIG. 2, and playback controls 158 such as a play button, stop button, skip to next track, begin previous track, etc. When the tether 152 is disconnected from earbuds 160 and 162, the earbuds 160 and 162 may function similarly to the earbuds 102 and 104 as shown and discussed with reference to FIG. 3. In other words, when the tether 152 is disconnected from the earbuds 160 and 162, the earbuds 160 and 162 may receive a wireless signal 136 (FIG. 3) from a media device 134 (FIG. 3) using a master/slave or other arrangement as described above.

Figure 6:
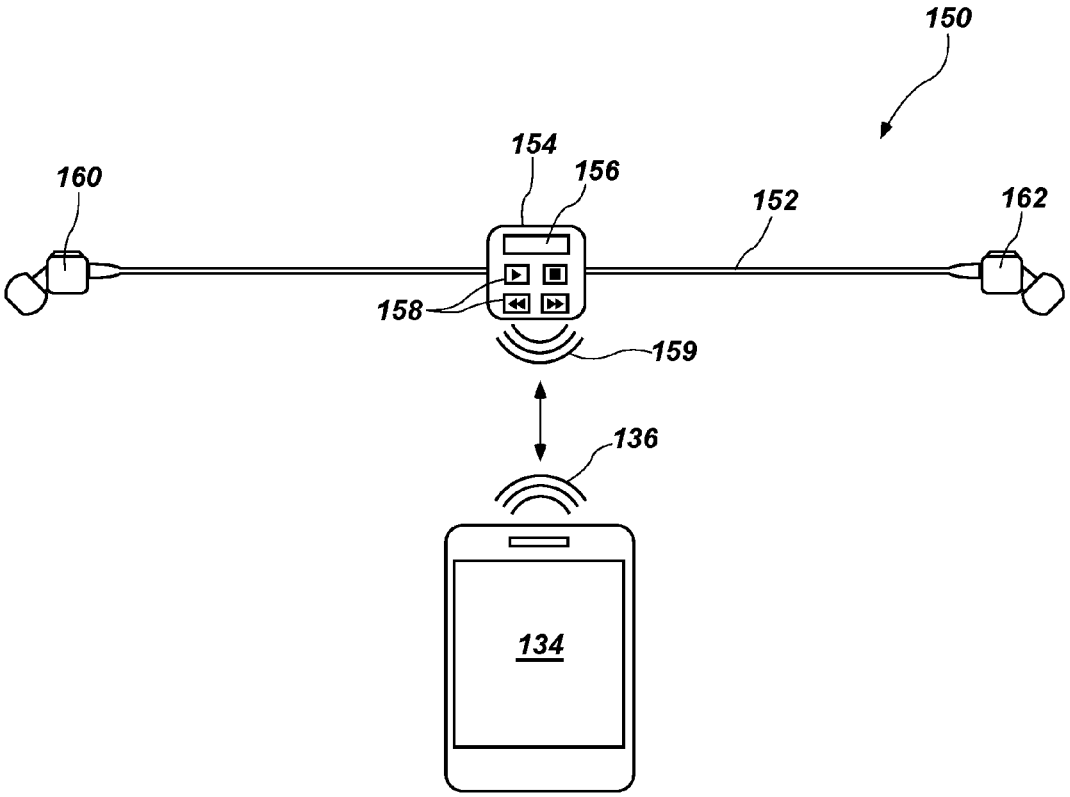
FIG. 6 is a schematic diagram showing an operational configuration of the earbud system of FIG. 5.

When the tether 152 is connected to the earbuds 160 and 162, the wireless earbud system 150 may operate as shown and described in connection with FIG. 6. A media device 134 may broadcast a wireless signal 136 containing audio data as described above in connection with FIG. 3. An RF receiver similar to RF receiver 126 shown in connection with FIG. 2 within the electronic control unit 154 may receive the wireless signal 136. The wireless signal may be processed (e.g., decoded) by the DAC in the electronic control unit 154 to provide one or more analog audio channels (e.g., left and right stereo audio channels). The left and right analog audio channel signals may be directed to respective earbuds 160 and 162 through conductors (not shown) within the tether 152. The analog audio signals may be amplified by audio amplifiers within the earbuds 160 and 162 similar to audio amplifier 130 described above in connection with FIG. 2. Additionally or alternatively, the electronic control unit 154 may include one or more audio amplifiers configured to amplify the analog audio signals to a level suitable to drive audio drivers (e.g., audio transducers 118 described in connection with FIG. 2). Such driver-level signals may be transferred through conductors within the tether 152 and fed directly to audio drivers within the earbuds 160 and 162. In some embodiments, one or more conductors in the tether 152 may function as an antenna to enhance reception of the wireless signal 136 by the RF receiver within the electronic control unit 154.

The playback controls 158 on the electronic control unit 154 may be configured to generate signals that may be transmitted wirelessly from the electronic control unit 154 to the media device 134 to control playback of audio tracks from the media device 134. For example, operation of the playback controls 158 may generate a wireless signal 159 broadcast from an RF transmitter (not shown) within the electronic control unit 154. The media device 134 may receive the wireless signal and alter audio playback as directed by the user's operation of the playback controls 158.

In some embodiments, the playback controls may be buttons arranged on the electronic control unit 154. In other embodiments, the playback controls may be operated by, for example, manipulating (e.g., squeezing) the tether 152. For example, at least a portion of the tether 152 may be configured to generate a voltage signal (e.g., by changing resistance) when squeezed by the user.

In some embodiments, the wireless earbuds 160 and 162, the electronic control unit 154, or both may be configured to collect information from the user and wirelessly transmit the information to the media device 134. For example, the wireless earbuds 160 and 162 may include sensors configured to sense biometric feedback such as heart rate or body temperature, sensors configured to sense movement (e.g., accelerometers), or other sensors. Information collected by these sensors may be transmitted wirelessly to the media device 134, where it may be organized and processed to provide information (e.g., a heart rate graph, number of steps taken, etc.) to be displayed to the user, posted to social media websites, or similarly employed.

When operating in the configuration described with reference to FIG. 6, certain limitations of some wireless earbuds may be mitigated. For example, at times, some wireless earbuds may suffer from uneven playback between earbuds, e.g., when the playback of left and right audio channels is not suitably synchronized and timing discrepancies between left and right audio channels are audibly noticeable. When connected by the tether 152, synchronization between the left and right channels can be maintained with high accuracy, at least because the left and right channels are transmitted by the same wireless signal 136. Moreover, as the batteries contained within the individual wireless earbuds (e.g., battery 122 (FIG. 2)) must be relatively small and lightweight to ensure that the wireless earbuds remain in the user's ear during activity, some wireless earbuds may have insufficient battery life for extended periods of use. When connected by the tether 152, the battery 156 in the electronic control unit 154 may provide significant additional operating time to the wireless earbuds. Finally, connecting the wireless earbuds 160 and 162 with the tether 152 may prevent loss of a single wireless earbud, particularly during physical activity of the user (e.g., jogging, cycling, etc.). Because the tether 152 is removable, the wireless earbuds 160 and 162 can be used without the tether and the electronic control unit 154 at times when such operation is desired.

Figure 7A:
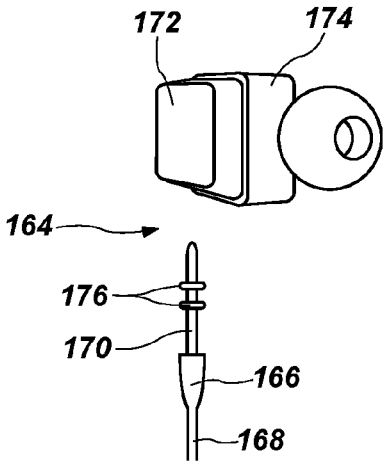
FIGS. 7A and 7B are perspective views of an earbud and a detachable connector according to an embodiment of the disclosure.
Figure 7B:
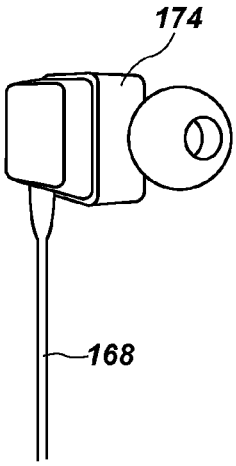

FIGS. 7A through 10B show various implementations of detachable connectors (e.g., detachable connectors 114 and 116 as described in connection with FIG. 1) according to embodiments of the disclosure. FIG. 7A shows an embodiment of a detachable connector 164 similar to that described with reference to FIG. 1. A distal end 166 of a tether 168 may include a plug 170 configured to be inserted within a recess (e.g., a bore, hole, receptacle, etc.) in a housing 172 of a wireless earbud 174. The plug 170 may include resilient flanges 176 configured to form an interference fit against walls of the recess to retain the plug 170 within the recess, thereby retaining the wireless earbud 174 on the tether 168, as shown in FIG. 7B.

Figure 8A:
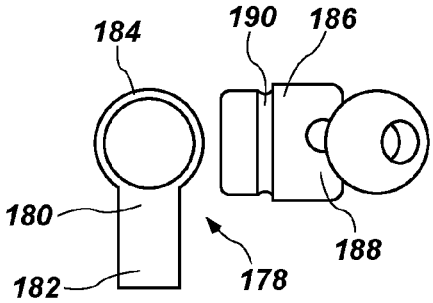
FIGS. 8A and 8B are perspective views of an earbud and a detachable connector according to another embodiment of the disclosure.
Figure 8B:
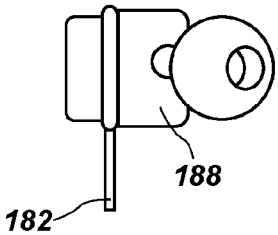

FIGS. 8A and 8B show another embodiment of a detachable connector 178. In this embodiment, a distal end 180 of a tether 182 includes a loop 184 of resilient material such as a flexible polymer. A housing 186 of a wireless earbud 188 includes a peripheral groove 190. The loop 184 may fit at least partially within the peripheral groove 190 to retain the wireless earbud 188 on the tether 182, as shown in FIG. 8B.

Figure 9A:
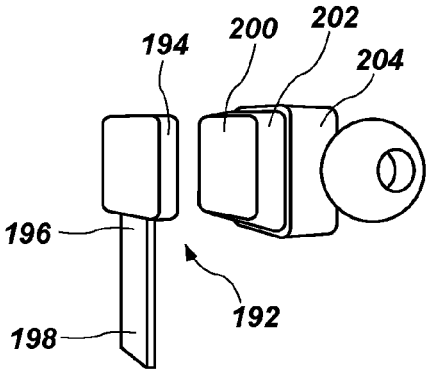
FIGS. 9A and 9B are perspective views of an earbud and a detachable connector according to yet another embodiment of the disclosure.
Figure 9B:
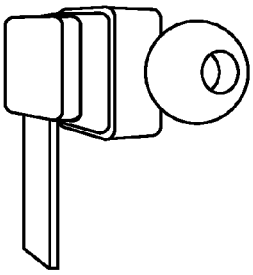

FIGS. 9A and 9B show another embodiment of a detachable connector 192. The detachable connector 192 includes a magnetic interface 194 positioned at a distal end 196 of a tether 198. A complementary magnetic interface 200 is disposed on a housing 202 of a wireless earbud 204. One or both of the magnetic interface 194 and the complementary magnetic interface 200 may include one or more permanent physical magnets such as ceramic magnets, rare earth magnets, etc. In some embodiments, one of the magnetic interface 194 and the complementary magnetic interface 200 may include magnetic material while the other of the magnetic interface 194 and the complementary magnetic interface 200 may include ferromagnetic material. Magnetic attraction between the magnetic interface 194 and the complementary magnetic interface 200 may retain the distal end 196 of the tether 198 to the housing 202 of the wireless earbud 204, as shown in FIG. 9B.

Figure 10A:
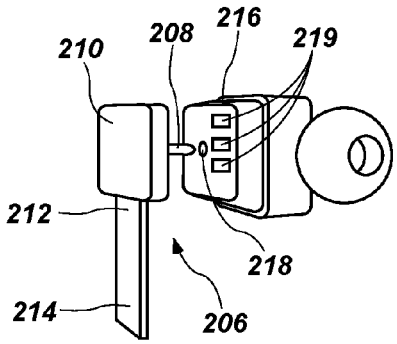
FIGS. 10A and 10B are perspective views of an earbud and a detachable connector according to yet another embodiment of the disclosure.
Figure 10B:
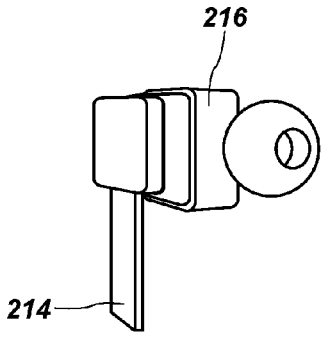

FIGS. 10A and 10B show yet another embodiment of a detachable connector 206. In this embodiment, the detachable connector 206 includes a pin 208 extending from a connection interface 210 on a distal end 212 of a tether 214. A wireless earbud housing 216 may include a recess 218 into which the pin 208 may be inserted. An interference fit between the pin 208 and the recess 218 may retain the tether 214 to the wireless earbud housing 216, as shown in FIG. 10B. Referring again to FIG. 10A, one or more electrically conductive contacts 219 may be disposed on the wireless earbud housing 216, and corresponding electrically conductive contacts (not shown) may be disposed on the connection interface 210. When the pin 208 is fully inserted within the recess 218, the electrically conductive contacts 219 may be brought into contact with the corresponding electrically conductive contacts of the connection interface 210, thereby connecting electrical circuitry within the wireless earbud housing 216 with electrical conductors in the tether 214. The electrically conductive contacts 219 and the corresponding electrically conductive contacts on the connection interface 210 may enable transfer of electrical signals between, e.g., the electronic control unit 154 (FIG. 5) and wireless earbuds 160 and 162 (FIG. 5) as described above.

While three (3) conductive contacts 219 are shown above in FIG. 10A, more than three, or less than three, conductive contacts 219 may be employed, depending on the configuration of the wireless earbuds and the functionality of the tether 214 and the electronic control unit 154 and the required number of discrete electrical pathways therebetween. Furthermore, conductive contacts similar to conductive contacts 219 may be used in connection with any of the detachable connectors (e.g., detachable connectors 164, 178, 192, 206) shown and described above. In other words, inclusion of conductive contacts is not limited to the specific embodiment of the detachable connector shown in FIGS. 10A and 10B.

Figure 11:
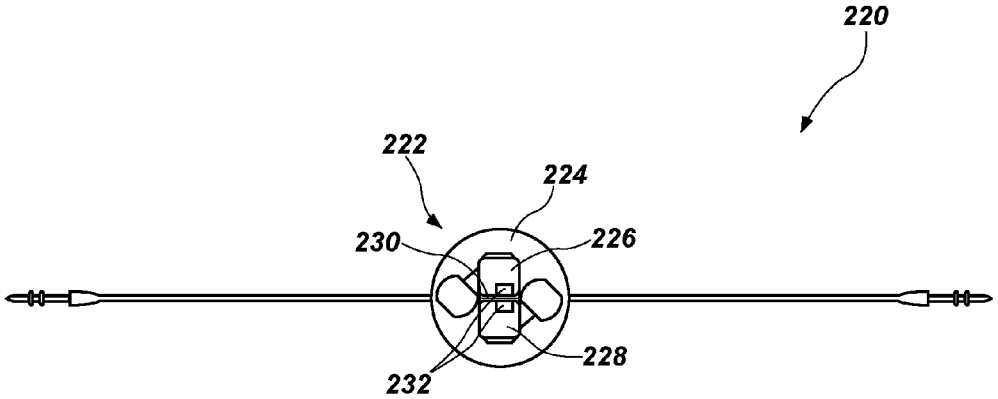
FIG. 11 is a plan view of yet another embodiment of an earbud system according to the disclosure.

FIG. 11 illustrates another embodiment of a wireless earbud system 220 in accordance with the present disclosure. The wireless earbud system 220 includes an electronic control unit 222 with a housing 224 configured to accept wireless earbuds 226 and 228 for storage and/or charging. In other words, the housing 224 of the electronic control unit 222 may include a recessed area with a profile at least partially matching the shape of the wireless earbuds 226 and 228 such that the wireless earbuds can be positioned at least partially within the housing 224. Electrical contacts (not shown) may be disposed within the housing 224 and positioned to make contact with electrical contacts (e.g., conductive contacts 219 described in connection with FIG. 10A) on one or both of the wireless earbuds 226 and 228 to charge batteries (e.g., battery 122 discussed above in connection with FIG. 2) within the wireless earbuds 226 and 228 using power from a battery within the electronic control unit 222 (e.g., battery 156 as discussed above in connection with FIG. 5) or a charging cable attached to the electronic control unit 222 and plugged into a charging port 149 (FIG. 4). For example, when the electronic control unit 222 is not attached to a charging cable, the batteries 122 within the earbuds may be charged by the battery 156 within the electronic control unit 222. When the electronic control unit 222 is attached to a charging cable, the batteries 122 and the battery 156 may charge simultaneously.

In some embodiments, the wireless earbuds 226 and 228 may attach to one another at an interface 230. For example, interface 230 may be a magnetic connection interface, e.g., similar to that described above in connection with FIGS. 9A and 9B. In other embodiments, the interface 230 may include mechanical connectors, such as tabs or pins and complementary slots or receptacles, etc.

The wireless earbuds 226 and 228 may each include a power switch 232 disposed on or adjacent to the interface 230. The power switch 232 may be configured to automatically power off each wireless earbuds 226, 228 when the wireless earbuds 226, 228 are connected at the interface 230, and to automatically power on the wireless earbuds when the wireless earbuds are detached from one another at the interface 230. The power switches 232 may prevent excessive power consumption when the earbuds are not in use and thus improve (e.g., maximize) battery life. The power switches 232 may be mechanical (e.g., plunger) switches or switches without moving parts, such as magnetic switches (e.g., hall effect switches) that change conductivity based on the presence of a magnetic field (e.g., a magnetic field associated with magnets of a magnetic connection interface between the wireless earbuds 226 and 228).

Figure 12A:
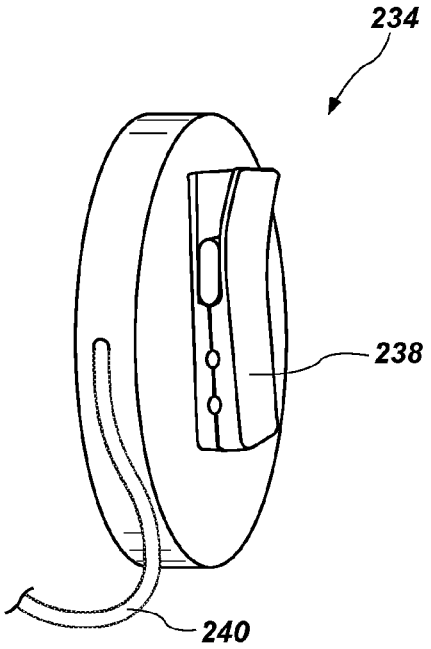
FIGS. 12A and 12B are perspective views of an electronic control unit according to an embodiment of the disclosure.
Figure 12B:
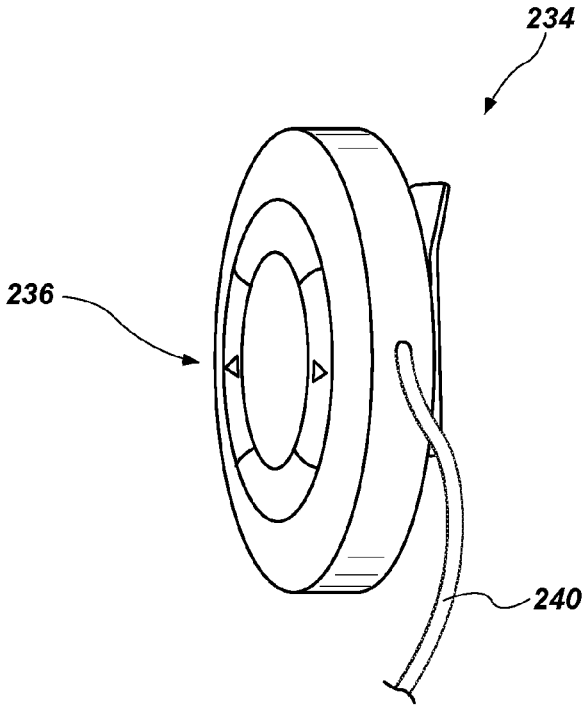

FIGS. 12A and 12B illustrate another embodiment of an electrical control unit 234 according to the present disclosure. The electrical control unit 234 may include playback controls 236 (FIG. 12B), such as play, stop, next track, and previous track buttons. The electrical control unit 234 may also include a clip, e.g., a spring-loaded clip 238 (FIG. 12A) configured to attach to a user's clothing, e.g., collar, placket, lapel, etc., for convenience. The electrical control unit 234 may include a tether 240 similar to, e.g., the tether 152 described above with reference to FIG. 5. The electrical control unit 234 may include functionality similar to the electronic control unit 154 described with reference to FIG. 5.

In some embodiments, the wireless earbud system 100 (FIG. 1), 138 (FIG. 4), 150 (FIG. 5, 6), or 220 (FIG. 11) may include software executable by the media device 134 (FIG. 3). For example, such software may include a graphical user interface (GUI) for display on a display screen of the media device 134. The GUI may include information related to the battery charge in each earbud, the battery charge in the electronic control unit 154 (FIG. 5), 234 (FIGS. 12A and 12B), playback mode (e.g., master-slave configuration or direct transmission to both earbuds as discussed in connection with FIG. 3), and other operational parameters of the earbud system.

Additional non-limiting example embodiments of the disclosure are set forth below.

Embodiment 1

A wireless earbud system, comprising: a first earbud assembly and a second earbud assembly, each of the first earbud assembly and the second earbud assembly comprising: a housing; an audio driver disposed within the housing; and a wireless receiving unit operatively coupled to the audio driver, the wireless receiving unit configured to receive a wireless data signal and drive the audio driver based on audio data transmitted in the wireless data signal; and a tether with a first end and a second end, wherein the first end of the tether is configured to removably couple to the first earbud assembly by a first detachable connector, and wherein the second end of the tether is configured to removably couple to the second earbud assembly by a second detachable connector.

Embodiment 2

The wireless earbud system of Embodiment 1, wherein each of the first detachable connector and the second detachable connector comprise electrical contacts operatively coupling a control unit in the tether with the first earbud assembly and the second earbud assembly.

Embodiment 3

The wireless earbud system of Embodiment 2, wherein the first earbud assembly comprises a first earbud battery and the second earbud assembly comprises a second earbud battery, wherein the control unit comprises a control unit battery, and wherein one or both of the first earbud battery and the audio driver in the first earbud assembly, and one or both of the second earbud battery and the audio driver in the second earbud assembly, are configured to draw electrical power from the control unit battery when the first end of the tether is coupled to the first earbud assembly and the second end of the tether is coupled to the second earbud assembly.

Embodiment 4

The wireless earbud system of Embodiment 2 or Embodiment 3, wherein the control unit in the tether comprises a wireless receiver configured to receive a wireless data signal from a media device and transmit an audio signal through the tether directly to the audio drivers of the first and second earbud assemblies through electrical conductors when the first and second ends of the tether are respectively coupled with the first and second earbud assemblies.

Embodiment 5

The wireless earbud system of any one of Embodiments 1 through 4, wherein the first detachable connector and the second detachable connector each comprise a peripheral groove in a portion of the first and second respective earbud housings and first and second resilient loops at the first and second respective ends of the tether, and wherein the first and second resilient loops are configured to fit at least partially within a respective one of the peripheral grooves to retain the first and second ends of the tether to the first and second respective earbud housings.

Embodiment 6

The wireless earbud system of any one of Embodiments 1 through 4, wherein the first detachable connector and the second detachable connector each comprise a magnetic interface on each of the first and second ends of the tether and a complementary magnetic interface on each of the first and second earbud housings.

Embodiment 7

The wireless earbud system of any one of Embodiments 1 through 4, wherein the first detachable connector and the second detachable connector each comprise a plug on each of the first and second ends of the tether configured for insertion within a respective complimentary recess disposed in each of the first and second earbud housings.

Embodiment 8

The wireless earbud system of any one of Embodiments 1 through 7, wherein the wireless receiving unit in the first earbud assembly and the wireless receiving unit in the second earbud assembly are each configured to receive a wireless signal from a media device and to send a wireless signal to the wireless receiving unit in the other of the first earbud assembly and the second earbud assembly.

Embodiment 9

The wireless earbud system of any one of Embodiments 1 through 8, wherein at least one of the first earbud assembly and the second earbud assembly comprise a sensor configured to sense biometric feedback, and wherein at least one of the wireless receiving unit in the first earbud assembly and the wireless receiving unit in the second earbud assembly are configured to transmit a wireless data signal based on the biometric feedback to a media device.

Embodiment 10

A wireless earbud system, comprising: a first earbud assembly and a second earbud assembly, each of the first earbud assembly and the second earbud assembly comprising: an audio driver; a wireless receiving unit operatively coupled to the audio driver, the wireless receiving unit configured to receive a wireless data signal; and an earbud battery configured to supply power to one or both of the audio driver and the wireless receiving unit; and a tether comprising: a first end with a first detachable connector configured to mechanically and electrically couple the first end of the tether to the first earbud assembly, a second end with a second detachable connector configured to mechanically and electrically couple the second end of the tether to the second earbud assembly; and an electronic control unit disposed intermediate the first end of the tether and the second end of the tether, the electronic control unit comprising: a wireless unit configured to receive a wireless data signal from a media device and to transmit an audio signal based on the wireless data signal through electrical conductors in the tether to the first and second earbud assemblies when the first and second earbud assemblies are coupled to the first and second ends of the tether, respectively; and an electronic control unit battery configured to supply power to the wireless unit.

Embodiment 11

The wireless earbud system of Embodiment 10, wherein the electronic control unit battery is configured to charge the first earbud battery when the first end of the tether is coupled to the first earbud assembly and to charge the second earbud battery when the second end of the tether is coupled to the second earbud assembly.

Embodiment 12

The wireless earbud system of Embodiment 10 or Embodiment 11, wherein the electronic control unit battery is configured to supply power to operate at least one of the first earbud audio driver and the first earbud wireless receiving unit when the first end of the tether is coupled to the first earbud assembly, and to supply power to operate at least one of the second earbud audio driver and the second wireless receiving unit when the second end of the tether is coupled to the second earbud assembly.

Embodiment 13

The wireless earbud system of any one of Embodiments 10 through 12, wherein the electronic control unit comprises one or more playback controls, and wherein the wireless unit is configured to transmit playback instructions from the playback controls to a media device.

Embodiment 14

The wireless earbud system of Embodiment 13, wherein the one or more playback controls comprise one or more buttons corresponding to one or more of playback instructions to play, stop, and proceed to a different audio track.

Embodiment 15

The wireless earbud system of any one of Embodiments 10 through 14, wherein the electronic control unit comprises a housing configured to store the first earbud assembly and the second earbud assembly.

Embodiment 16

The wireless earbud system of Embodiment 15, wherein the first earbud assembly and the second earbud assembly are configured to couple to one another for storage in the electronic control unit housing.

Embodiment 17

The wireless earbud system of Embodiment 16, wherein the first earbud assembly and the second earbud assembly each comprise a complementary magnetic coupler, each complementary magnetic coupler configured to interact to couple the first earbud assembly to the second earbud assembly.

Embodiment 18

The wireless earbud system of Embodiment 16 or Embodiment 17, wherein the first earbud assembly and the second earbud assembly each include electronic switches configured to power off the first earbud assembly and the second earbud assembly when the first earbud assembly and the second earbud assembly are coupled to one another.

Embodiment 19

The wireless earbud system of Embodiment 18, wherein the electronic switches are configured to automatically power on the first earbud assembly and the second earbud assembly when the first earbud assembly is decoupled from the second earbud assembly.

Embodiment 20

A method of forming a wireless earbud system, the method comprising: forming an electronic control unit comprising a wireless unit, a battery, and a tether; forming first and second wireless earbud assemblies; configuring first and second ends of the tether to removably couple to the first and second wireless earbud assemblies; configuring one or both of the first and second wireless earbud assemblies to receive a wireless signal from a media device and to drive audio drivers in the first and second wireless earbud assemblies with an audio signal based on data received from the media device when the first and second ends of the tether are decoupled from the first and second wireless earbud assemblies; and configuring the wireless unit of the electronic control unit to receive a wireless signal from the media device and to drive the audio drivers in the first and second wireless earbud assemblies through electrical conductors disposed within the tether with an audio signal based on data received wirelessly from the media device when the first and second ends of the tether are respectively coupled to the first and second earbud assemblies.

While certain illustrative embodiments have been described in connection with the figures, those of ordinary skill in the art will recognize and appreciate that embodiments encompassed by the disclosure are not limited to those embodiments explicitly shown and described herein. Rather, many additions, deletions, and modifications to the embodiments described herein may be made without departing from the scope of embodiments encompassed by the disclosure, such as those thereinafter claimed, including legal equivalents. In addition, features from one disclosed embodiment may be combined with features of another disclosed embodiment while still being encompassed within the scope of embodiments encompassed by the disclosure as contemplated by the inventors.

What is claimed is:

1. A wireless earbud system, comprising:

a first earbud assembly and a second earbud assembly, each of the first earbud assembly and the second earbud assembly comprising:

a housing;

an audio driver disposed within the housing; and a wireless receiving unit operatively coupled to the audio driver, the wireless receiving unit configured to receive a wireless data signal and drive the audio driver based on audio data transmitted in the wireless data signal; and a tether with a first end, a second end, and a control unit located between the first end and the second end, wherein the first end of the tether is configured to removably couple to the first earbud assembly by a first detachable connector, wherein the second end of the tether is configured to removably couple to the second earbud assembly by a second detachable connector, and wherein at least one of the first earbud assembly and the second earbud assembly is configured to operate as a master and communicate directly with a media device when the first end and the second end of the tether are disconnected from the first earbud assembly and the second earbud assembly, and wherein the control unit is configured to operate as [a] *the* master and communicate directly with the media device, with the first earbud assembly and the second earbud assembly operating as slaves and communicating directly with the control unit, when the first end of the tether is connected to the first earbud assembly and the second end of the tether is connected to the second earbud assembly.

2. The wireless earbud system of claim 1, wherein each of the first detachable connector and the second detachable connector comprise electrical contacts operatively coupling the control unit in the tether respectively with the first earbud assembly and the second earbud assembly.

3. The wireless earbud system of claim 2, wherein the first earbud assembly comprises a first earbud battery and the second earbud assembly comprises a second earbud battery, wherein the control unit comprises a control unit battery, and wherein one or both of the first earbud battery and the audio driver in the first earbud assembly, and one or both of the second earbud battery and the audio driver in the second earbud assembly, are configured to draw electrical power from the control unit battery when the first end of the tether is coupled to the first earbud assembly and the second end of the tether is coupled to the second earbud assembly.

4. The wireless earbud system of claim 2, wherein the control unit in the tether comprises a wireless receiver configured to receive a wireless data signal from a media device and transmit an audio signal through the tether directly to the audio drivers of the first and second earbud assemblies through electrical conductors when the first and second ends of the tether are respectively coupled with the first and second earbud assemblies.

5. The wireless earbud system of claim 1, wherein the first detachable connector and the second detachable connector each comprise a peripheral groove in a portion of the first and second respective earbud housings and first and second resilient loops at the first and second respective ends of the tether, and wherein the first and second resilient loops are configured to fit at least partially within a respective one of the peripheral grooves to retain the first and second ends of the tether to the first and second respective earbud housings.

6. The wireless earbud system of claim 1, wherein the first detachable connector and the second detachable connector each comprise a magnetic interface on each of the first and second ends of the tether and a complementary magnetic interface on each of the first and second earbud housings.

7. The wireless earbud system of claim 1, wherein the first detachable connector and the second detachable connector each comprise a plug on each of the first and second ends of the tether configured for insertion within a respective complimentary recess disposed in each of the first and second earbud housings.

8. The wireless earbud system of claim 1, wherein the wireless receiving unit in the first earbud assembly and the wireless receiving unit in the second earbud assembly are each configured to selectively operate as a master and receive a wireless signal directly from a media device and to send a wireless signal to the wireless receiving unit in the other of the first earbud assembly and the second earbud assembly.

9. The wireless earbud system of claim 1, wherein at least one of the first earbud assembly and the second earbud assembly comprise a sensor configured to sense biometric feedback, and wherein at least one of the wireless receiving unit in the first earbud assembly and the wireless receiving unit in the second earbud assembly are configured to transmit a wireless data signal based on the biometric feedback to a media device.

10. A wireless earbud system, comprising:

a first earbud assembly and a second earbud assembly, each of the first earbud assembly and the second earbud assembly comprising:

an audio driver;

a wireless receiving unit operatively coupled to the audio driver, the wireless receiving unit configured to receive a wireless data signal; and an earbud battery configured to supply power to one or both of the audio driver and the wireless receiving unit; and a tether comprising:

a first end with a first detachable connector configured to mechanically and electrically couple the first end of the tether to the first earbud assembly, a second end with a second detachable connector configured to mechanically and electrically couple the second end of the tether to the second earbud assembly; and an electronic control unit disposed intermediate the first end of the tether and the second end of the tether, the electronic control unit comprising:

a wireless unit configured to receive a wireless data signal from a media device and to transmit an audio signal based on the wireless data signal through electrical conductors in the tether to the first and second earbud assemblies when the first and second earbud assemblies are coupled to the first and second ends of the tether, respectively; and an electronic control unit battery configured to supply power to the wireless unit;

wherein at least one of the first earbud assembly and the second earbud assembly is configured to operate as a master and communicate directly with a media device when the first end and the second end of the tether are disconnected from the first earbud assembly and the second earbud assembly, and wherein the control unit is configured to operate as [a] *the* master and communicate directly with the media device, with the first earbud assembly and the second earbud assembly operating as slaves and communicating directly with the control unit, when the first end of the tether is connected to the first earbud assembly and the second end of the tether is connected to the second earbud assembly.

11. The wireless earbud system of claim 10, wherein the electronic control unit battery is configured to charge the first earbud battery when the first end of the tether is coupled to the first earbud assembly and to charge the second earbud battery when the second end of the tether is coupled to the second earbud assembly.

12. The wireless earbud system of claim 10, wherein the electronic control unit battery is configured to supply power to operate at least one of the first earbud audio driver and the first earbud wireless receiving unit when the first end of the tether is coupled to the first earbud assembly, and to supply power to operate at least one of the second earbud audio driver and the second wireless receiving unit when the second end of the tether is coupled to the second earbud assembly.

13. The wireless earbud system of claim 10, wherein the electronic control unit comprises one or more playback controls, and wherein the wireless unit is configured to transmit playback instructions from the playback controls to a media device.

14. The wireless earbud system of claim 13, wherein the one or more playback controls comprise one or more buttons corresponding to one or more of playback instructions to play, stop, and proceed to a different audio track.

15. The wireless earbud system of claim 10, wherein the electronic control unit comprises a housing configured to store the first earbud assembly and the second earbud assembly.

16. The wireless earbud system of claim 15, wherein the first earbud assembly and the second earbud assembly are configured to couple to one another for storage in the electronic control unit housing.

17. The wireless earbud system of claim 16, wherein the first earbud assembly and the second earbud assembly each comprise a complementary magnetic coupler, each complementary magnetic coupler configured to interact to couple the first earbud assembly to the second earbud assembly.

18. The wireless earbud system of claim 16, wherein the first earbud assembly and the second earbud assembly each include electronic switches configured to power off the first earbud assembly and the second earbud assembly when the first earbud assembly and the second earbud assembly are coupled to one another.

19. The wireless earbud system of claim 18, wherein the electronic switches are configured to automatically power on the first earbud assembly and the second earbud assembly when the first earbud assembly is decoupled from the second earbud assembly.

20. A method of forming a wireless earbud system, the method comprising:

forming an electronic control unit comprising a wireless unit, a battery, and a tether;

forming first and second wireless earbud assemblies;

configuring first and second ends of the tether to removably couple to the first and second wireless earbud assemblies;

configuring one or both of the first and second wireless earbud assemblies to operate in a master mode and receive a wireless signal directly from a media device and to drive audio drivers in the first and second wireless earbud assemblies with an audio signal based on data received directly from the media device when the first and second ends of the tether are decoupled from the first and second wireless earbud assemblies;

configuring the wireless unit of the electronic control unit to operate in [a] *the* master mode and receive a wireless signal directly from the media device and to drive the audio drivers in the first and second wireless earbud assemblies through electrical conductors disposed within the tether with an audio signal based on data received directly wirelessly from the media device when the first and second ends of the tether are respectively coupled to the first and second earbud assemblies; and configuring both of the first and second wireless earbud assemblies to operate in a slave mode and receive the wireless signal directly from the wireless unit of the electronic control unit and to drive audio drivers in the first and second wireless earbud assemblies with an audio signal based on data received directly from the wireless unit of the electronic control unit when the first and second ends of the tether are respectively coupled to the first and second wireless earbud assemblies.

*21. A wireless earbud system, comprising:*

*a first earbud assembly and a second earbud assembly, each of the first earbud assembly and the second earbud assembly comprising:*

*a housing:*

*an audio driver disposed within the housing; and*

*a wireless receiver operatively coupled to the audio driver, the wireless receiver configured to receive a wireless data signal and drive the audio driver responsive to audio data transmitted in the wireless data signal utilizing circuitry and/or software routines of the first earbud assembly or second earbud assembly;*

*wherein the circuitry and/or the software routines of each of the first earbud assembly and the second earbud assembly is configured to switch the wireless receiver of each of the first earbud assembly and the second earbud assembly between operating as a master to receive a first wireless data signal from a media device and operating as a slave to receive a second data signal from the first earbud assembly or second earbud assembly comprising the wireless receiver configured as the master on a regular, periodic basis.*

*22. The wireless earbud system of claim 21, wherein the circuitry and/or the software of the first earbud assembly is configured to separate the audio data into a first audio channel and a second audio channel, to send the first audio channel to the audio driver of the first earbud assembly, and to send the second audio channel to the second earbud assembly when the first earbud assembly is operating as the master.*

*23. The wireless earbud system of claim 22, wherein the circuitry and/or the software of the first earbud assembly is configured to separate the audio data into a right audio channel and a second audio channel, to send a first of the right and left audio channels to the audio driver of the first earbud assembly, and to send a second of the right and left audio channels to the second earbud assembly utilizing the wireless receiver of the first earbud assembly when the first earbud assembly is operating as the master.*

*24. The wireless earbud system of claim 21, wherein the wireless receiver of the first earbud assembly comprises a wireless transmitter and wherein the wireless receiver of the second earbud assembly is configured to receive the second data signal from the first earbud assembly wirelessly when the first earbud assembly is operating as the master.*

*25. The wireless earbud system of claim 21, wherein each of the first earbud assembly and the second earbud assembly comprises a battery, and wherein the wireless circuitry and/or the software routines of each of the first earbud assembly and the second earbud assembly is further configured to switch the wireless receiver of each of the first earbud assembly and the second earbud assembly between operating as the slave and operating as the master based on remaining charge in each battery.*

*26. The wireless earbud system of claim 21, wherein the wireless receiver comprises a radio-frequency receiver operatively coupled to a digital-to-analog converter.*

*27. The wireless earbud system of claim 21, wherein at least one of the first earbud assembly or the second earbud assembly comprises a sensor configured to sense biometric feedback, and wherein at least one of the wireless receiver in the first earbud assembly or the wireless receiver in the second earbud assembly is configured to transmit a wireless data signal comprising the biometric feedback to the media device.*

*28. The wireless earbud system of claim 21, further comprising a tether having a first end and a second end, the first end of the tether configured to removably couple to the first earbud assembly by a first detachable connector, the second end of the tether configured to removably couple to the second earbud assembly by a second detachable connector.*

*29. The wireless earbud system of claim 28, wherein each of the first earbud assembly and the second earbud assembly comprises a detachable connector configured to receive detachable connectors of the tether, each detachable connector free of an electrical connection configured to establish electrical communication between the first earbud assembly and the second earbud assembly.*

*30. The wireless earbud system of claim 28, wherein each of the first earbud assembly and the second earbud assembly comprises a detachable connector configured to receive detachable connectors of the tether, each detachable connector comprising an electrical connection configured to establish electrical communication between the first earbud assembly and the second earbud assembly via the tether.*

*31. The wireless earbud system of claim 30, wherein each detachable connector of the first earbud assembly and the second earbud assembly comprises one of a magnetic interface configured for magnetic attachment to a corresponding magnetic interface of the tether or a recess sized and shaped to receive a plug or a pin of the tether therein.*

*32. A wireless earbud system, comprising:*

*a first earbud assembly and a second earbud assembly, each of the first earbud assembly and the second earbud assembly comprising:*

*a housing;*

*an audio driver disposed within the housing: and*

*a wireless receiver operatively coupled to the audio driver, the wireless receiver configured to receive a wireless data signal and drive the audio driver responsive to audio data transmitted in the wireless data signal;*

*wherein the wireless receiver of the first earbud assembly is configured to intermittently operate as a master to receive a first wireless data signal from a media device and the wireless receiver of the second earbud assembly is configured to intermittently operate as a slave to receive a second data signal from the first earbud assembly;*

*wherein the wireless receiver of the second earbud assembly is configured to intermittently operate as the master to receive a first wireless data signal from the media device and the wireless receiver of the first earbud assembly is configured to intermittently operate as the slave to receive a second data signal from the second earbud assembly; and*

*wherein circuitry and/or software routines of each of the first earbud assembly and the second earbud assembly is configured to switch the wireless receiver of each of the first earbud assembly and the second earbud assembly between operating as the master and operating as the slave on a regular, periodic basis.*

*33. The wireless earbud system of claim 32, wherein the circuitry and/or software routines of the first earbud assembly is configured to separate the audio data into a first audio channel and a second audio channel, to send the first audio channel to the audio driver of the first earbud assembly, and*

*to send the second audio channel to the second earbud assembly when the first earbud assembly is operating as the master.*

*34. The wireless earbud system of claim 32, wherein each of the first earbud assembly and the second earbud assembly comprises a battery, and wherein the circuitry and/or software routines of the first earbud assembly is further configured to switch operation the wireless receiver of the first earbud assembly between master and slave, and the wireless receiver of the second earbud assembly is further configured to switch the wireless receiver of the second earbud assembly to operate between slave and master based on remaining charge in each battery.*

*35. The wireless earbud system of claim 32, further comprising a tether having a first end and a second end, the first end of the tether configured to removably couple to the first earbud assembly by a first detachable connector, the second end of the tether configured to removably couple to the second earbud assembly by a second detachable connector.*

*36. The wireless earbud system of claim 35, wherein each of the first earbud assembly and the second earbud assembly comprises a detachable connector configured to receive detachable connectors of a tether, each detachable connector free of an electrical connection configured to establish electrical communication between the first earbud assembly and the second earbud assembly.*

*37. The wireless earbud system of claim 35, wherein each of the first earbud assembly and the second earbud assembly comprises a detachable connector configured to receive detachable connectors of the tether, each detachable connector comprising an electrical connection configured to establish electrical communication between the first earbud assembly and the second earbud assembly via the tether.*

*38. The wireless earbud system of claim 37, wherein each detachable connector of the first earbud assembly and the second earbud assembly comprises one of a magnetic interface configured for magnetic attachment to a corresponding magnetic interface of the tether or a recess sized and shaped to receive a plug or a pin of the tether therein.*

* * * * *